United States Patent [19]

Horiuchi et al.

[11] 4,362,939
[45] Dec. 7, 1982

[54] METHOD AND APPARATUS FOR MEASUREMENT OF MOISTURE

[75] Inventors: Shoichi Horiuchi; Yoshihiro Sase, both of Katsuta, Japan

[73] Assignee: Hitachi, Ltd., Tokyo, Japan

[21] Appl. No.: 173,600

[22] Filed: Jul. 30, 1980

[30] Foreign Application Priority Data

Aug. 1, 1979 [JP] Japan .................................. 54-97346

[51] Int. Cl.³ ........................ G01N 23/00; G01T 3/00
[52] U.S. Cl. .............................. 250/358.1; 250/359.1; 250/390
[58] Field of Search .................... 250/358 R, 359, 360, 250/390, 391, 392

[56] References Cited

U.S. PATENT DOCUMENTS 3,431,415  3/1969  Stone et al. ..................... 250/358 R
3,524,062  8/1970  Rocoplan et al. .............. 250/358 R
3,786,251  1/1974  Kylin et al. ..................... 250/358 R

FOREIGN PATENT DOCUMENTS 1387007  3/1975  United Kingdom .

Primary Examiner—Alfred E. Smith
Assistant Examiner—Janice A. Howell
Attorney, Agent, or Firm—Antonelli, Terry and Wands

[57] ABSTRACT

A bulk material of grain, lump or any other form is irradiated with neutron and gamma radiation emitted from preferably a single radiation source, and preferably a single radiation detector detects the neutrons and gamma radiation transmitted through the bulk material, so that the moisture content of the bulk material can be accurately measured without being affected by the bulk density of the bulk material.

6 Claims, 5 Drawing Figures

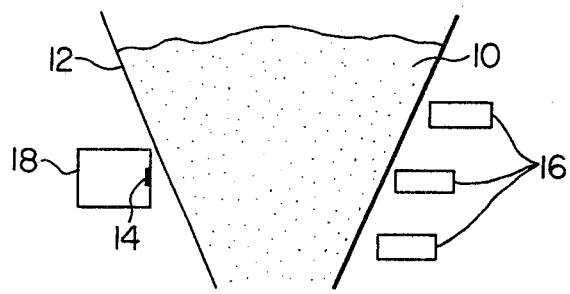
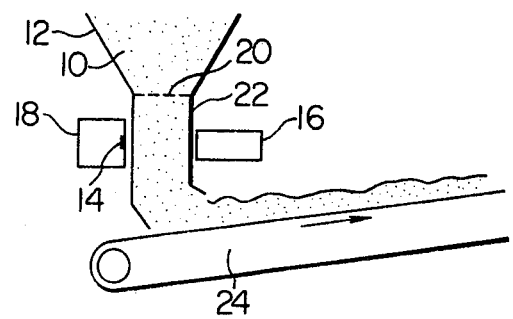
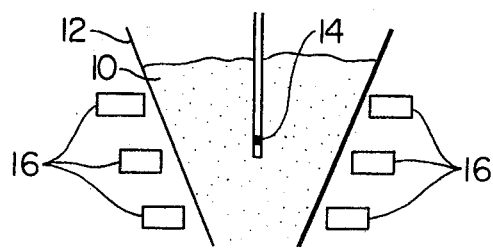
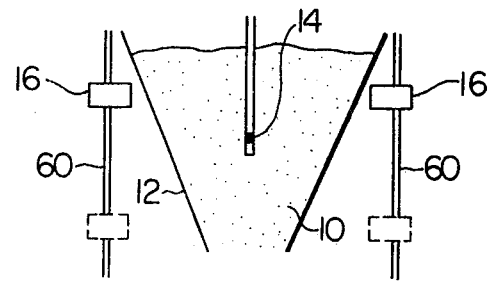

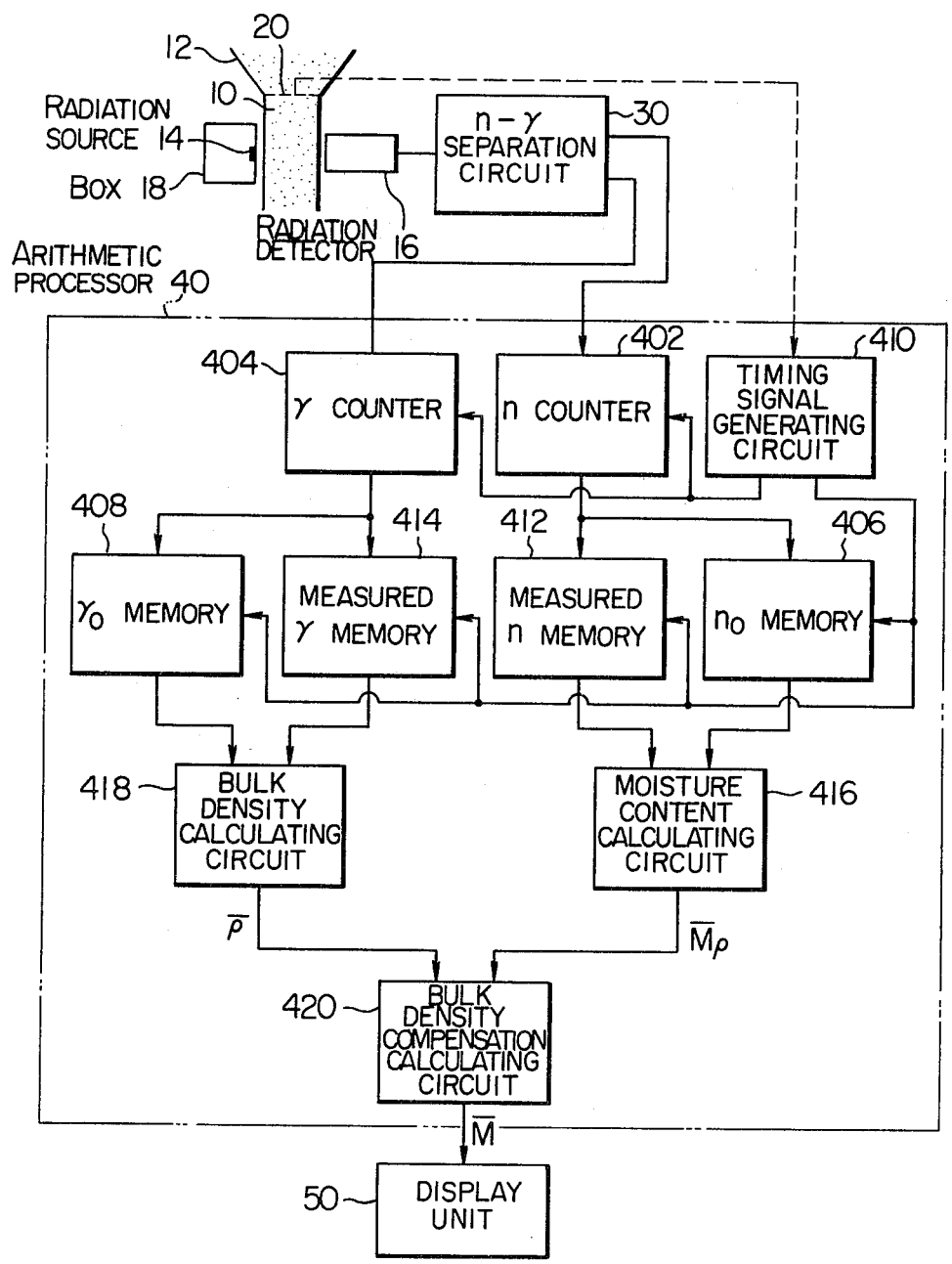

METHOD AND APPARATUS FOR MEASUREMENT OF MOISTURE

BACKGROUND OF THE INVENTION

This invention relates to a method and an apparatus for measuring the moisture content of bulk material in grain or lump form utilizing the scattering and absorption of radiation.

Control of moisture in a bulk material, for example, coke or sinter mix materials used in the steel industry is indispensible for the successful production of steel of good quality, since the coke ratio and the quality of the steel are dependent upon how the moisture content is controlled. For this purpose, a moisture meter or gauge of the scattering type utilizing the scattering of neutrons has hitherto been widely used for the measurement of the moisture content.

It is known that, in a method of moisture measurement in which the scattering of neutrons is only resorted to for the measurement of the moisture content of a bulk material, the rate of scattering of neutrons is affected not only by the moisture content of the bulk material, but also by the bulk density of the bulk material. The bulk density varies depending on the grain size distribution or moisture distribution of the bulk material, and it is therefore impossible to measure the actual bulk density. U.S. Pat. No. 3,786,251 discloses a method which reduces the influence of the bulk density on the measurement of the moisture content of a bulk material. In this U.S. patent, gamma radiation is employed in addition to the neutrons, and the measured value of gamma radiation is used to compensate the measured value of neutrons so as to reduce the influence of the bulk density on the result of moisture content measurement.

However, due to the fact that a neutron detector and a gamma detector are provided independently of each other in the system disclosed in U.S. Pat. No. 3,786,251, and the position measured by the neutron detector differs from that measured by the gamma detector, the value of the moisture content obtained by compensation has not always been accurate.

SUMMARY OF THE INVENTION

It is therefore a primary object of the present invention to provide a method and an apparatus for moisture measurement by which the moisture content of a bulk material can be measured more accurately than hitherto.

The present invention is featured by the fact that a radiation source radiating neutron and gamma radiation is employed, and a radiation detector capable of detecting both the neutrons and the gamma radiation is employed. Thus, since a single detector detects both the neutrons and the gamma radiation, the moisture content and the bulk density at the same position of a bulk material can be measured, and the result of measurement is therefore highly accurate. When independent radiation detectors are provided for detecting the neutrons and gamma radiation respectively as described hereinbefore, it is impossible to make measurement on the same point, and it is also necessary to maintain a considerable distance between the two detectors so as to prevent mutual interference. It is therefore preferable to prepare a single radiation source capable of emitting both the neutrons and the gamma radiation. As an alternative, the neutrons and the gamma radiation may be derived from independent radiation sources, respectively. In this case, however, it is necessary to dispose the neutron radiation source and the gamma radiation source in such a relation that they are as close to each other as possible. As a radiation source capable of emiting both the neutrons and the gamma radiation, $^{252}Cf$ is an example. As a radiation source emitting the neutrons only, $^{241}Am$-Be is an example, and as a radiation source emitting the gamma radiation only, $^{137}Cs$ and $^{60}Co$ are examples.

BRIEF DESCRIPTION OF THE DRAWINGS

FIG. 1 shows schematically an embodiment of the moisture measuring method according to the present invention.

FIG. 2 shows schematically another embodiment of the moisture measuring method according to the present invention.

FIG. 3 is a block diagram of an apparatus which puts the method shown in FIG. 2 into practice.

FIGS. 4 and 5 show schematically other embodiments of the moisture measuring method according to the present invention.

DESCRIPTION OF THE PREFERRED EMBODIMENTS

Referring to FIG. 1 showing an embodiment of the moisture measuring method according to the present invention, a radiation source 14 emitting fast neutron and gamma radiation is disposed on one side of a hopper 12 charged with a bulk material 10 whose moisture content is to be measured, and radiation detectors 16 capable of detecting both the fast neutrons and the gamma radiation are disposed on the other side of the hopper 12 opposite to the radiation source 14. The radiation source 14 is mounted in a box 18 having a sufficient shielding ability, and the fast neutrons and the gamma radiation emitted from the radiation source 14 pass through the hopper 12 and the bulk material 10 to be detected by the radiation detectors 16. Each of these radiation detectors 16 is composed of a stilbene scintillator or a liquid scintillator and a high-resolution photomultiplier so that it can detect both of the neutrons and the gamma radiation at any desired sensitivity. Employment of $^{252}Cf$, which is a spontaneously fissionable nuclide, as the radiation source 14 in the system of radiation transmission measurement type is most suitable since it emits a very large number of neutrons and the energy of the gamma radiation is high. It is the sole defect of $^{252}Cf$ that its half life is as short as about 2.7 years, and therefore, compensation for the decay becomes necessary. This decay can however be automatically compensated in a manner as described later.

The moisture content M of the bulk material 10 can be calculated from the equations described presently.

The measurement value of the neutrons is given by $$N_n = N_{no} e^{-(\mu_{n1}\rho_1 R + \mu_{n2}\rho_2 x)} \quad (1)$$

where $N_n$: counted value of transmitted neutrons $N_{no}$: counted value of transmitted neutrons in the absence of bulk material $\mu_{n1}$: mass absorption coefficient of bulk material (neutrons)

$\mu_{n2}$: mass absorption coefficient of water (neutrons)

$\rho_1$: bulk density of bulk material $\rho_2$: density of water
R: thickness of bulk material
x: moisture content expressed in terms of thickness of water The measured value of the gamma radiation is given by $$N_\gamma = N_{\gamma 0} e^{-(\mu_{\gamma 1}\rho_1 R + \mu_{\gamma 2}\rho_2 x)} \quad (2)$$

where
$N_\gamma$: counted value of transmitted gamma radiation
$N_{\gamma o}$: counted value of transmitted gamma radiation in the absence of bulk material
$\mu_\gamma 1$: mass absorption coefficient of bulk material (gamma radiation)
$\mu_\gamma 2$: mass absorption coefficient of water (gamma radiation)

The value of x is calculated from the equations (1) and (2) as follows:

$$x = \frac{\mu_{\gamma 1} l_n(N_{n0}/N_n) - \mu_{n1} l_n(N_{\gamma 0} - N_\gamma)}{\mu_{\gamma 1}\mu_{n2}\rho_2 - \mu_{n1}\mu_{\gamma 2}\rho_2} \quad (3)$$

The value of $\rho_1$ is calculated from the equation (2) as follows:

$$\rho_1 = \frac{l_n(N_{\gamma 0}/N_\gamma) - \mu_{\gamma 2}\rho_2 x}{\mu_{\gamma 1} R} \quad (4)$$

Therefore, the moisture content M of the bulk material 10 is expressed as $$M = \frac{x}{R\rho_1 + x} \times 100 \text{ (\% by weight)} \quad (5)$$

It will be apparent from the above equations that the moisture content M of the bulk material can be calculated on the basis of the value of the bulk density $\rho_1$ calculated at a constant thickness R of the bulk material. By the way, the value of transmitted neutrons $N_{no}$ and the value of transmitted gamma radiation $N_{65\ o}$ counted in the absence of the bulk material very depending on a decay of the radiation source 14 or a variation of the wall thickness of the hopper 12 due to wear, deposition of matters on the hopper wall, etc. However, the value of neutrons $N_{no}$ and the value of gamma radiation $N_{65\ o}$ transmitted through the hopper 12 before the bulk material 10 is charged into the hopper 12 are to be previously measured so as to facilitate the compensation of $N_{no}$ and $N_{65\ o}$ due to the decay of the radiation source or the variation of the wall thickness of the hopper.

In another embodiment of the present invention shown in FIG. 2, the position of moisture measurement is changed from that shown in FIG. 1. In FIG. 2, the moisture content is measured at a position of a discharge chute 22 of a hopper 12 by a single radiation detector 16 disposed opposite to a radiation source 14. A gate 20 opened to discharge a bulk material 10 through the discharge chute 22 onto a belt conveyor 24 which conveys the bulk material 10 toward the next station. Although the length of time required for a batch of the bulk material 10 to be discharged completely onto the belt conveyor 24 is limited by the moving speed of the belt conveyor 24, the required moisture measurement can be successfully carried out within the above length of time which is as long as about 30 seconds. The method shown in FIG. 2 is advantageous over that shown in FIG. 1 and can economically attain the desired object. It is a first advantage that the amount of radiation to be emitted from the radiation source 14 can be reduced since the distance between the radiation source 14 and the radiation detector 16 is smaller than that in FIG. 1 and the path of the radiation absorbed by the bulk material becomes shorter than that in FIG. 1. It is a second advantage that the single radiation detector 16 can participate in the moisture content measurement of the batch of the bulk material charged into the hopper since the entirety of the bulk material moves through the position of moisture measurement.

Practical means for putting the method shown in FIG. 2 into practice will be described with reference to FIG. 3.

Upon completion of weighing, the gate 20 is opened, and the batch of the bulk material 10 charged in the hopper 12 is discharged within a length of time of about 30 seconds. After the bulk material 10 has been completely discharged, the gate 20 is closed again. The next batch of the bulk material 10 is charged into the hopper 12, and weighing is done again. The bulk material is processed according to such a batch system in which the above cycle is repeated.

In the first step, the neutron and gamma radiation emitted from the radiation source 14 is directed toward the radiation detector 16 in the state in which the gate 20 is in its closed position and the bulk material 10 is not present in the discharge chute 22. In a neutron-gamma (n-γ) separating circuit 30 which is, for example, a pulse shape discrimination circuit, the neutrons and the gamma radiation are countably separated to be counted by a neutron (n) counter 402 and a gamma (γ) counter 404 respectively in an arithmetic processor 40. The counted values are stored in a neutron (no) memory 406 and a gamma (γo) memory 408 respectively. These values are counted and renewed for every batch to accomplish the function of so-called automatic zero calibration, so that the factors due to the variation of the wall thickness of the hopper, the variation of the amount of deposits on the hopper wall and the decay of the radiation source can be fully compensated. A timing signal generating circuit 410 generates a timing signal in response to the opening and closure of the gate 20 and applies the timing signal to various blocks.

Then, when the gate 20 is opened to start discharge of the bulk material 10, the neutron and gamma radiation which is transmitted through the bulk material 10 enters the radiation detector 16. The amount of the neutrons transmitted through the bulk material 10 is dependent upon the moisture content and bulk density of the bulk material 10, while that of the gamma radiation is dependent upon the bulk density of the bulk material 10. The values of the neutrons and gamma radiation counted until the complete discharge of the bulk material 10 are stored in a measured neutron (n) memory 412 and a measured gamma (γ) memory 414 respectively. The data stored in the measured n memory 412 and the auto-zero data stored in the no memory 406 are supplied to a moisture content calculating circuit 416 which calculates the mean moisture content $\overline{M}\rho$. Similarly, the data stored in the measured γ memory 414 and the auto-zero data stored in the γo memory 408 are supplied to a bulk density calculating circuit 418 which calculates the mean bulk density $\overline{\rho}$. Then, on the basis of the value of $\overline{\rho}$, the bulk density is compensated in a bulk density compensation calculating circuit 420 which calculates the true mean moisture content $\overline{M}$ which is displayed on a display unit 50.

According to the embodiment shown in FIGS. 2 and 3, the radiation source emitting the neutron and gamma radiation and the associated radiation detector are disposed on the opposite sides of the discharge chute of the hopper, so that the entirety of the batch of the bulk material charged into the hopper can be completely measured as the bulk material moves down past the point of moisture measurement, so that the mean moisture content of the entire batch of the bulk material can be calculated. Further, the neutrons and the gamma radiation transmitted through the discharge chute of the hopper in the absence of the bulk material in the discharge chute are measured to store the so-called auto-zero values which are used as the reference data during later calculations. Therefore, variations of the hopper wall thickness and hopper deposit amount can be automatically compensated, and the results of measurement are free from the influences of the wall thickness of the hopper and the amount of deposits on the hopper wall.

FIGS. 4 and 5 show other embodiments of the present invention. As shown in FIGS. 4 and 5, the radiation source 14 may be inserted into the hopper 12, and the neutron and gamma radiation emitted from the radiation source 14 may be detected by radiation detectors 16 disposed outside the hopper 12. In this case, the total moisture content of the bulk material 10 is measured while the bulk material 10 stays within the hopper 12. A plurality of radiation detectors 16 may be disposed outside the hopper 12 as shown in FIG. 4, or a single radiation detector 16 may be disposed to replace each set of three detectors 16 shown in FIG. 4 and may be arranged to be guided along a guide rail 60 as shown in FIG. 5. The arrangement shown in FIG. 5 reduces the required number of radiation detectors 16.

It will be understood from the foregoing description that the present invention comprises a radiation source emitting fast neutron and gamma radiation and a radiation detector capable of detecting both the neutrons and the gamma radiation, so that the neutrons and the gamma radiation can be directed toward the same point of a bulk material whose moisture content is to be measured, and the moisture content can be accurately measured without being affected by the bulk density of the bulk material.

We claim:

1. A method of measuring the moisture content of a bulk material comprising the steps of emitting fast neutrons and gamma radiation at a point on one side of the bulk material, detecting both the fast neutrons and the gamma radiation at the same point on the other side of the bulk material opposite to the point of emission of said radiation, separating and counting the fast neutrons and gamma radiation transmitted through the bulk material, and calculating the moisture content of the bulk material on the basis of the counted values of the fast neutrons and gamma radiation.

2. A method as claimed in claim 1, wherein said radiation is emitted by radiation source means in the form of a single source which emits both the fast neutrons and the gamma radiation, and $^{252}$Cf is used as said single radiation source.

3. A method of measuring the moisture content of a bulk material comprising the steps of charging the bulk material into a container, disposing radiation source means for emitting fast neutrons and gamma radiation on one side of a discharge chute portion of said container, disposing radiation detector means for detecting both the fast neutrons and the gamma radiation on the other side of said discharge chute portion opposite to said radiation source means, separating and counting the fast neutrons and the gamma radiation while the bulk material is moving through said discharge chute portion, and calculating the moisture content of the bulk material on the basis of the counted values of the fast neutrons and gamma radiation.

4. A method as claimed in claim 3, further comprising the step of previously counting the values of the fast neutrons and gamma radiation in the absence of the bulk material in said discharge chute portion of said container to obtain an auto-zero value which is used as a reference value in the calculation of moisture content.

5. An apparatus for measuring the moisture content of a bulk material comprising a radiation source for emitting fast neutrons and gamma radiation, a radiation detector for detecting both the fast neutrons and the gamma radiation, the bulk material being disposed between said radiation source and said radiation detector, separating circuit means for separating the output from said radiation detector into a neutron output and a gamma output, a neutron counter and a gamma counter for counting the neutron output and the gamma output from said separating circuit means, first neutron memory means and first gamma memory means for storing the outputs of said neutron counter and said gamma counter, respectively, derived in the absence of the bulk material, second neutron memory means and second gamma memory means for storing the outputs of said neutron counter and said gamma counter, respectively, derived in the presence of the bulk material, a circuit for calculating the moisture content of the bulk material on the basis of the outputs of said first and second neutron memories, a circuit for calculating the bulk density of the bulk material on the basis of the outputs of said first and second gamma memories, and a circuit for compensating the output of said moisture content calculating circuit on the basis of the output of said bulk density calculating circuit.

6. A method of measuring the moisture content of a bulk material in a container comprising:
(a) emitting fast neutrons and gamma radiation at a first point on one side of a discharge chute of the container,
(b) detecting both the fast neutrons and the gamma radiation at a second point on the other side of the discharge chute opposite to the point of emission of said radiation in the absence of the bulk material in the container,
(c) separating and counting the fast neutrons and the gamma radiation detected in step (b),
(d) detecting both the fast neutrons and the gamma radiation at said second point in the presence of the bulk material in said container,
(e) separating and counting the fast neutrons and the gamma radiation detected in said step (d), and
(f) calculating the moisture content of the bulk material on the basis of the counted values of the fast neutrons and gamma radiation in said steps (c) and (e).

* * * * *